United States Patent [19]
Westerdal

[11] 4,314,553
[45] Feb. 9, 1982

[54] EARPLUG AND EARPLUG SET

[75] Inventor: Roland Westerdal, Great Falls, Va.

[73] Assignee: Bilsom AB, Billesholm, Sweden

[21] Appl. No.: 64,861

[22] Filed: Aug. 8, 1979

[51] Int. Cl.³ .............................................. A61F 11/02
[52] U.S. Cl. ................................ 128/152; 128/201.18;
        D24/67; 181/135; 179/1 ST; 179/107 E;
        179/182 R
[58] Field of Search .................... 128/151, 152, 201.18,
        128/245, 239, 207.18; D24/67; 181/135, 129,
        130, 131; 215/355; 179/1 ST, 107 E, 182 R

[56] References Cited
U.S. PATENT DOCUMENTS

| | | | |
|---|---|---|---|
| D. 89,947 | 5/1933 | Cohn | D24/67 |
| D. 241,881 | 11/1979 | Peterson et al. | D24/67 |
| D. 245,202 | 7/1977 | Asker | D24/67 |
| 968,008 | 8/1910 | Waller | 128/152 |
| 2,492,183 | 12/1949 | Rosenblatt | 128/152 |
| 3,259,128 | 7/1966 | Leight | 128/152 |
| 3,301,253 | 1/1967 | Glorig | 128/152 |
| 3,415,246 | 12/1968 | Hill | 128/152 |
| 3,618,600 | 11/1971 | Douglass | 128/152 |
| 3,871,372 | 3/1975 | Bivins | 128/152 |
| 3,935,401 | 1/1976 | Shore et al. | 181/135 X |
| 4,167,185 | 9/1979 | Lewis | 128/206.24 |

FOREIGN PATENT DOCUMENTS

| | | | |
|---|---|---|---|
| 692013 | 8/1964 | Canada | 215/355 |
| 456207 | 9/1925 | Fed. Rep. of Germany . | |
| 64824 | 12/1955 | France | 215/355 |
| 74535 | 12/1960 | France | 128/151 |

OTHER PUBLICATIONS
Clora-Kapor, Abtegma., Brochure page, 720828 ers.

Primary Examiner—Henry J. Recla
Attorney, Agent, or Firm—Sandler & Greenblum

[57] ABSTRACT

An earplug comprising a stem portion and a front portion mounted on the stem portion. The front portion is conically shaped and disposed such that the inner surface of the front portion is spaced from the stem portion. At least one spacing member may be provided which is adapted to space the interior surface of the front portion from the stem portion.

The earplug may further comprise an axial bore therein adapted to receive a cord such that two of the earplugs may be connected by the cord so as to form a set.

17 Claims, 6 Drawing Figures

EARPLUG AND EARPLUG SET

RELATED MATERIALS

Applicant respectfully directs attention to Design application Ser. No. 64,882 filed concurrently herewith.

BACKGROUND OF THE INVENTION

1. Field of the Invention

The invention relates to an earplug commonly used by insertion within the human ear to reduce the amount of noise heard.

2. Description of Prior Art

Earplugs are well-known and are used both in industry and by individuals. The purpose of earplugs is to reduce noise exposure while providing a maximum of comfort to the user.

U.S. Pat. No. 3,301,243 to Glorig discloses an ear protector comprising a generally mushroom-shaped tip or head mounted on a stem. The stem itself is surrounded by a sleeve. A head set is used to bias two of the earplugs into the ears of the user.

U.S. Pat. No. 3,618,600 to Douglass allegedly represents an improvement over the Glorig earplug and attempts to provide greater comfort to the user. The stem portion of the plug is modified so as to increase its effective cross-sectional area thereby reducing the pressure on the ear in terms of force per unit area. The stem is modified by tapering it so as to provide a bulge as the plug is forced against the ear.

German Pat. No. 456,207 discloses an earplug having a mushroom-shaped tip as well as a stem having an orifice extending therethrough.

Swedish Pat. No. 399,178 discloses an earplug set connected by a cord. The front portion of the earplug is provided with an orifice in its outer surface.

U.S. Pat. No. 968,008 to Waller discloses a "noise arrestor" comprising plugs or buttons which are maintained within the ear for purposes of reducing sound transmission. FIG. 9 of the patent illustrates a plug having what would appear to be a hemispherical shape. A headband is used to maintain the plug within the ear.

U.S. Pat. No. 2,492,183 to Rosenblatt discloses an acoustic device made of a soft rubber having a mushroom-shaped head which is solid in cross-section.

U.S. Pat. Design No. 245,202 to Asker again discloses an earplug having a mushroom-shaped head.

Finally, U.S. Pat. No. 3,415,246 to Hill (FIGS. 7-10) illustrates an ear fitting having a generally mushroom-shaped tip or head. The fitting is used for purposes of transmitting sound rather than arresting sound transmission. The fitting is provided with an orifice through which the sound may pass.

SUMMARY OF THE INVENTION

It is an object of the invention to provide an earplug which is both effective yet comfortable.

It is a further object of the invention to provide an earplug which suitably fits a wide range of the population such that essentially only one size of the plug is necessary to fit the vast majority of users.

The objects are fulfilled by means of the earplug of the invention which comprises a stem portion and a front portion mounted on the stem portion. The front portion is conically-shaped and arranged such that the inner surface of the front portion is spaced from the stem portion. At least one spacing member may be provided which is adapted to space the interior surface of the front portion from the stem portion.

The front portion of the plug is appropriately shaped so as to comfortably fit within the ear of the user and is in effect an ear contact portion which flares outwardly from one end of the stem towards the other end thereof.

In a preferred embodiment of the invention the front or ear contact portion has a substantially continuous surface. By this it is meant that there are substantially no orifices or the like provided along the outer surface of the front portion.

The stem portion itself is preferably in the form of a cylindrical shaft having first and second ends. The front portion is preferably mounted on the first end while the second end may comprise a bore adapted to receive a cord therein.

The purpose of the cord is to connect two of the earplugs so as to form a set. The cord itself may preferably be inserted directly into the bore arranged within the stem.

A plurality of spacing members are provided each of which is preferably in the form of a radially-extending flange arranged between the stem and the inner surface of the front portion. The spacing members may be equidistantly arranged around the shaft.

The spacing members contribute to the ability of the earplug to be used in a wide range of ear canal sizes. The supports work particularly well in medium, large and extra large ear canals to prevent collapse of the mushroom or conical shaped front portion thus providing an effective seal and improved sound attenuation. By virtue of the fact that the front portion is flared outwardly as a result of the support members, a large contact area is provided within the ear canal thus providing extraordinary comfort to the user. The plurality of spacing members extend between the front and stem portions, thereby spacing the interior surface of the front portion from the stem portion both prior to and during insertion of the ear plug into one of the ear canals. These members are shown as extending generally radially.

The cord, string, or other connecting means used to connect the two plugs to form a set preferably comprises a sheath or the like around each of its end portions such that the sheathed cord fits easily but securely within the axial bore provided in the stem of the plug.

According to a particularly advantageous embodiment of the invention the earplug is formed of unitary construction, i.e., one piece construction, and does not require the assembly of additional elements onto the sheath or plug itself.

DESCRIPTION OF PREFERRED EMBODIMENTS

Figure 1:
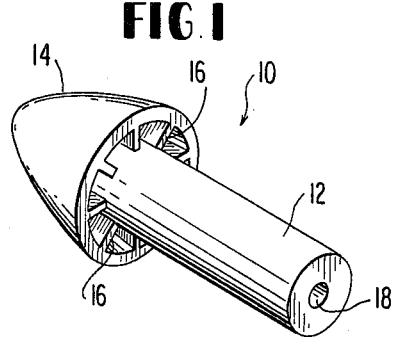
FIG. 1 illustrates a rear perspective view of an earplug of the invention.

FIG. 1 illustrates an earplug 10 having a shaft portion 12 and an ear contact or front portion 14. As illustrated, the front portion is convex has a substantially conical or mushroom shape. The term conical as used throughout the application and claims is not to be taken in its strictest literal sense and includes both conical and paraboloid shapes as well as any other shapes which are similar to those illustrated.

As may be further seen in FIG. 1, a plurality of spacing members 16 may be provided which serve to space the inner surface of the concave front portion of the plug from the stem so as to provide a more comfortable and efficient seal with the interior of the ear and improved sound attenuation when inserted therein.

Figure 2:
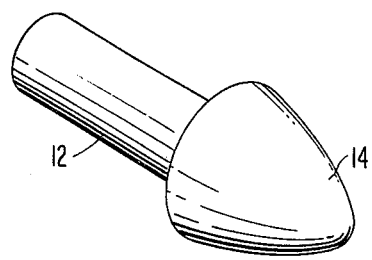
FIG. 2 illustrates a front perspective view of an earplug of the invention.

FIG. 2 further illustrates the preferably continuous outer surface of the front portion. By this it is meant that there are substantially no orifices provided along the outer surface of the front portion.

Figure 6:
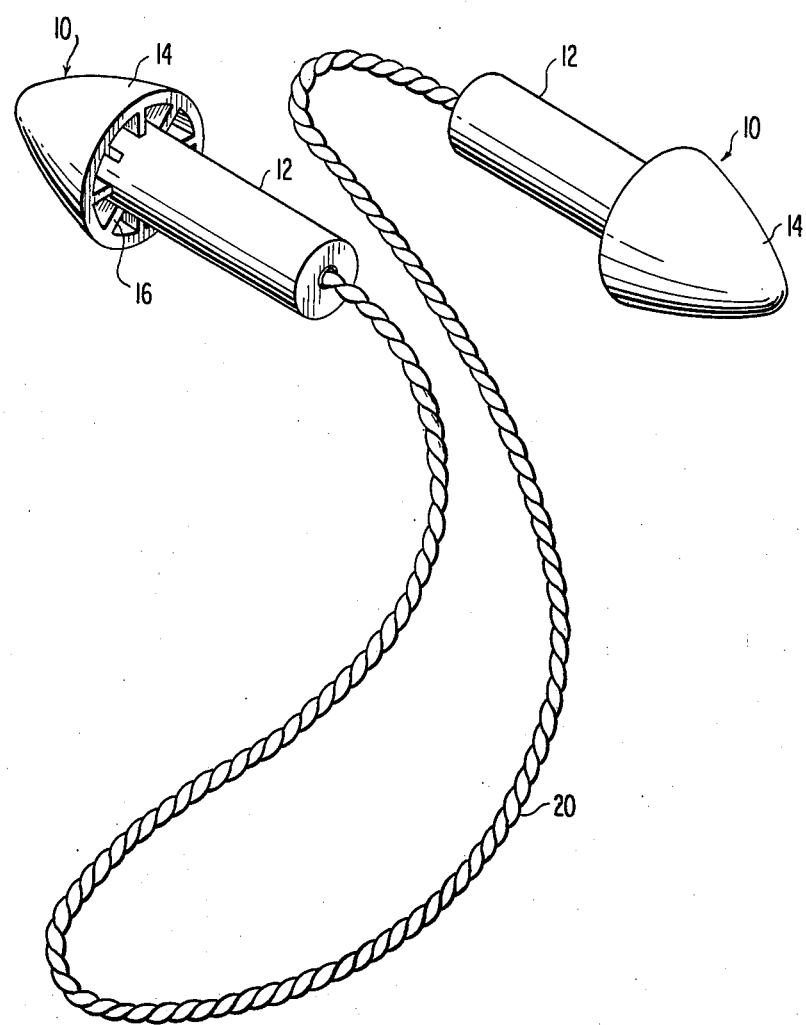
FIG. 6 illustrates an earplug set.

FIG. 3 once again illustrates the plug and axially bore 18. The purpose of the axial bore is to receive a cord or other connecting member therein so that the plug may be connected to another plug to form a set. (FIG. 6).

Figure 3:
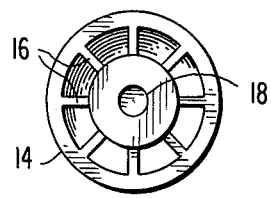
FIG. 3 is a rear view of the earplug of the invention.

As may be clearly seen from FIG. 3, the spacer members 16 are preferably equidistantly spaced from one another and extend radially in the form of flanges between the stem and the interior surface of the front portion of the earplug.

Figure 4:
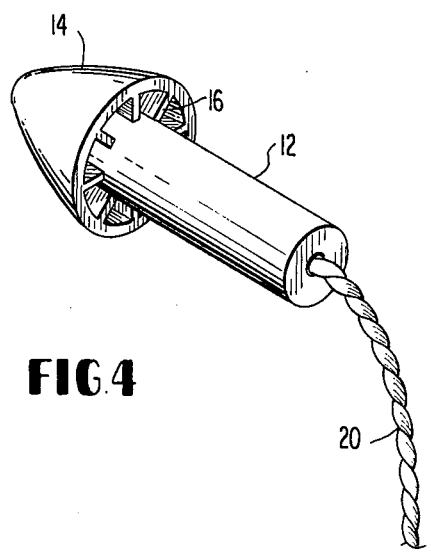
FIG. 4 is a rear perspective view similar to FIG. 1 illustrating the insertion of a cord into the earplug stem.

FIG. 4 illustrates the plug having a cord 20 inserted therein. The cord may be made of any conventional materials such as string, plastic cord, filament, and the like.

Figure 5:
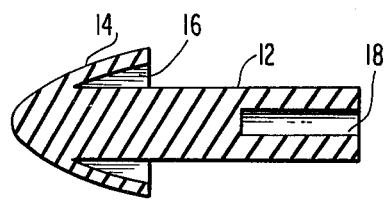
FIG. 5 is a cross-sectional view of the inventive earplug showing the cord with its sheath prior to insertion into the plug.
Figure 5:
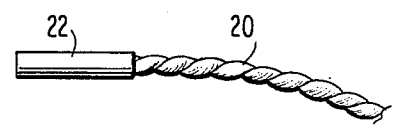

As may be seen from FIG. 5, the cord 20 is provided with a plastic sheath 22 whereby the plastic sheath may be easily yet securely inserted within the axial bore 18 provided in shaft 12 of the earplug.

The plug may be made of any suitable material but is preferably made out of 45 durometer silicon rubber so as to provide an efficient and comfortable fit within the user's ear.

While one advantage of the invention is that a single size earplug will fit the majority of the population, it is quite obviously possible to provide other sizes for people having extra small or extra extra large ear canals.

Although the invention has been described with respect to specific means and materials, it is to be understood that the invention is not limited to those means and materials specifically disclosed but extends to cover all embodiments covered by the claims.

What is claimed is:

1. An earplug adapted in size to fit within and to be inserted into a wide range of human ear canals comprising:
   (a) a stem portion;
   (b) a front portion mounted on said stem portion, said front portion being a conically shaped flexible wall member having a convex outer surface and a concave inner surface, said stem portion extending within said wall member and connected to the inner surface, and disposed such that a space exists between the inner surface of said front portion and said stem portion both prior to and during insertion of said earplug canal; and
   (c) means comprising a plurality of spacing members extending between said inner surface of said front portion and said stem portion for spacing the inner surface of the front portion from said stem portion both prior to and during insertion of said ear plug into an ear canal.

2. The earplug as defined by claim 1 wherein said front portion has a continuous outer surface.

3. The earplug as defined by claim 2 wherein said stem portion is in the form of a shaft having a first and second end, said inner surface of said front portion being attached to said first end and said second end comprising a bore adapted to receive a cord therein.

4. The earplug as defined by claim 3 wherein said spacing members comprise radially extending flanges.

5. The earplug as defined by claim 4 wherein said spacing members are spaced equidistantly around said shaft.

6. An earplug set comprising two of said earplugs of claim 1 and a cord connected between the stem portion of each respective earplug.

7. The earplug set as defined by claim 6 wherein each of said stem portions of said earplugs comprises a bore adapted to receive one end of said cord.

8. The earplug set as defined by claim 7 wherein said cord comprises an annular sheath surrounding each end thereof fitted into said bore.

9. The earplug set as defined by claim 8 wherein said spacing members comprise a plurality of radially extending flanges.

10. The earplug as defined by claim 1 wherein said front portion is adapted to directly contact the interior of a human ear canal.

11. The earplug as defined by claim 1 adapted to comfortably fit within a human ear canal.

12. An earplug comprising an ear contact portion and a stem and being adapted in size to fit within and to be inserted into a wide variety of human ear canals, said ear contact portion having a flexible wall member with a convex outer surface and a concave inner surface and being connected to one end of said stem with said wall member flaring outwardly from said one end of said stem towards the other end of said stem such that a space exists between the inner surface and the stem both prior to and during insertion of said earplug into an ear canal, and means comprising a plurality of spacing members extending between said inner surface of said ear contact portion and said stem for spacing the inner surface of said ear contact portion from said stem both prior to and during insertion of said earplug into an ear canal.

13. The earplug as defined by claim 11 wherein said outer surface is substantially continuous.

14. The earplug as defined by claim 13 wherein said stem comprises an axial bore adapted to receive a cord therein.

15. The ear plug as defined by claim 12 wherein said spacing members comprise generally radially extending flanges.

16. A method of attenuating sound heard by humans, said method comprising the step of inserting an earplug adapted in size to fit within a wide range of human ear canals into the ear of a human, said ear plug comprising:
   (a) a stem portion;
   (b) a front portion mounted on said stem portion, said front portion being a conically shaped flexible wall member having a convex outer surface and a concave inner surface, said stem portion extending within said wall member and connected to the inner surface, and disposed such that a space exists between the inner surface of said front portion and said stem portion both prior to and during insertion of said earplug into an ear canal; and (c) means comprising a plurality of spacing members extending between said inner surface of said front portion and said stem portion for spacing the inner surface of the front portion from said stem portion both prior to and during insertion of said earplug into an ear canal.

17. A method as defined by claim 16 wherein said spacing members are generally radially extending flanges.

* * * * *

UNITED STATES PATENT AND TRADEMARK OFFICE
CERTIFICATE OF CORRECTION

PATENT NO. : 4,314,553

DATED : February 9, 1982

INVENTOR(S) : Roland WESTERDAL

It is certified that error appears in the above—identified patent and that said Letters Patent is hereby corrected as shown below:

Column 3, line 22, --extending-- should be inserted after "axially".

Signed and Sealed this

Fourth Day of May 1982

[SEAL]

Attest:

Attesting Officer

GERALD J. MOSSINGHOFF

Commissioner of Patents and Trademarks